United States Patent

Gaylord

Patent Number: 5,452,527
Date of Patent: Sep. 26, 1995

[54] SHOE FOR A FOOT CAST

[75] Inventor: John F. Gaylord, Jr., Charlotte, N.C.

[73] Assignee: Medical Specialties, Inc., Charlotte, N.C.

[21] Appl. No.: 16,770

[22] Filed: Feb. 11, 1993

[51] Int. Cl.[6] .................................................. A43B 3/00
[52] U.S. Cl. .............................. 36/110; 36/11.5; 602/23
[58] Field of Search ................. 36/110, 154, 7.1 R, 36/29, 11.5; 602/3, 23, 28, 29, 65

[56] References Cited

U.S. PATENT DOCUMENTS

| | | | |
|---|---|---|---|
| 2,278,626 | 4/1942 | Vasko | 36/8.5 |
| 2,598,217 | 5/1952 | Bronson | 36/110 |
| 3,021,846 | 2/1962 | Scholl | 36/154 |
| 3,160,963 | 12/1964 | Aaskov | 36/29 X |
| 3,566,487 | 3/1971 | Beightol | 36/2.5 |
| 3,584,402 | 6/1971 | Silverman | 36/11.5 |
| 3,613,674 | 10/1971 | Volz | 128/83.5 |
| 3,798,803 | 3/1974 | Kennedy | 36/11.5 |
| 3,802,424 | 4/1974 | Newell | 128/82 |
| 3,905,135 | 9/1975 | Debusk | 36/2.5 |
| 4,100,686 | 7/1978 | Sgarlato et al. | 36/29 |
| 4,178,703 | 12/1979 | Pols | 36/110 |
| 4,217,706 | 8/1980 | Vartanian | 36/110 |
| 4,265,033 | 5/1981 | Pols | 36/110 |
| 4,425,721 | 1/1984 | Spronken | 36/11.5 |
| 4,635,384 | 1/1987 | Huh et al. | 36/29 |
| 4,641,639 | 2/1987 | Padilla | 602/23 |
| 4,677,767 | 7/1987 | Darby | 36/110 X |
| 4,773,170 | 9/1988 | Moore | 36/110 |
| 4,899,468 | 2/1990 | Richbourg | 36/110 |
| 5,014,448 | 5/1991 | Perrone | 36/110 |
| 5,022,168 | 1/1991 | Jeppson, III et al. | 36/43 |
| 5,195,945 | 3/1993 | Sandvig et al. | 602/23 X |

FOREIGN PATENT DOCUMENTS 8904125  5/1989  WIPO ................................ 36/110

Primary Examiner—Paul T. Sewell
Assistant Examiner—Ted Kavanaugh
Attorney, Agent, or Firm—Bell, Seltzer, Park & Gibson

[57] ABSTRACT

A shoe to be worn on a foot cast for providing a more normal gait as the wearer of the cast walks, the shoe has a molded sole formed of a foam material, a shoe upper connected to the molded sole and adapted to extend around the foot cast, and straps connected to the shoe upper for securing the shoe upper and the molded sole on the foot cast. The molded sole is formed of integrally molded foam material wherein an upper portion thereof defines an innersole and a lower portion thereof defines an outersole. The innersole has a concave recess extending throughout major portions thereof and with the depth thereof being such as to receive lower portions of the foot cast and to permit the wearer thereof to have a gait corresponding substantially to that of a normal shoe. The outersole has a roughened outer surface for providing increased frictional resistance with the surface upon which the outersole contacts.

16 Claims, 2 Drawing Sheets

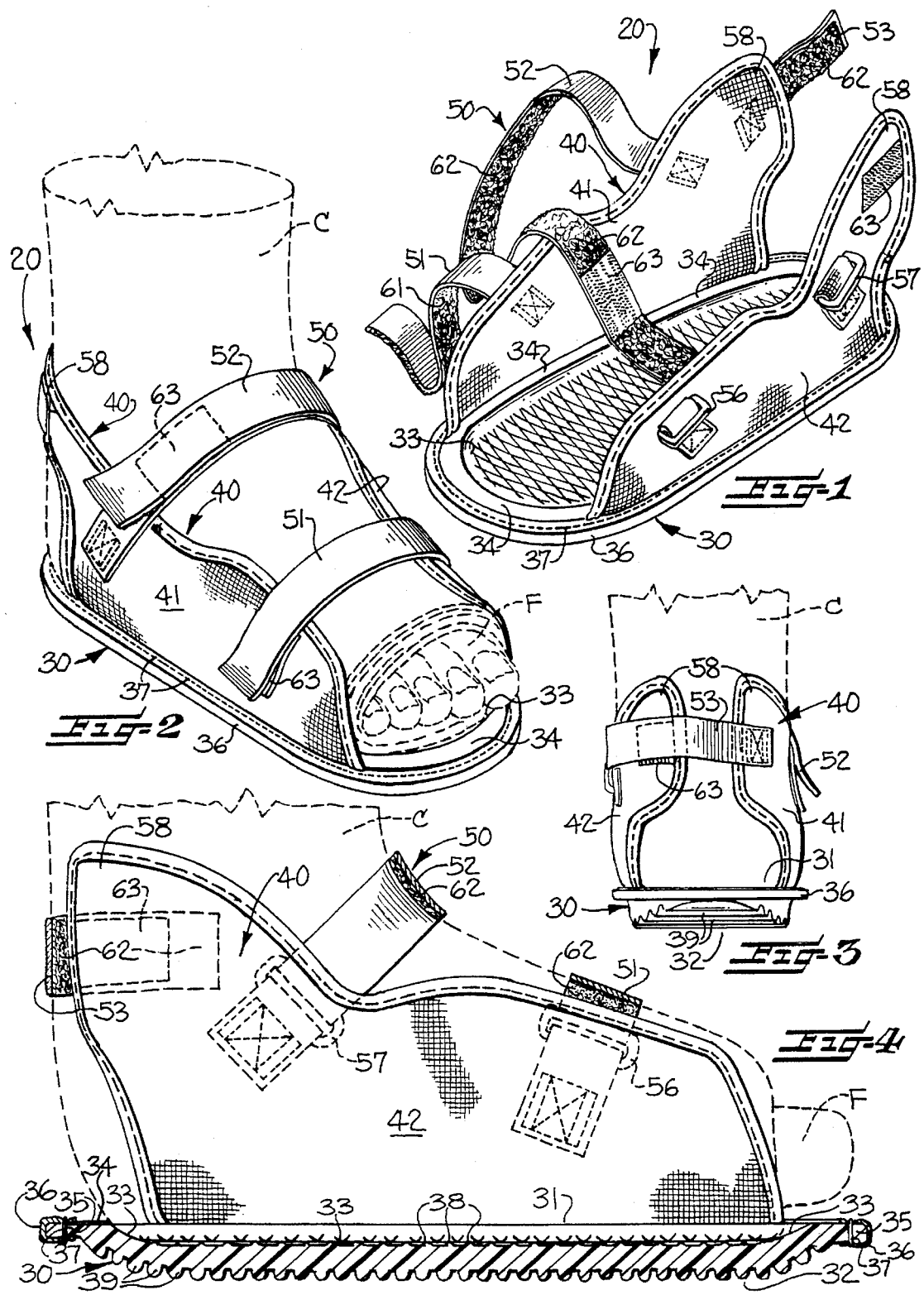

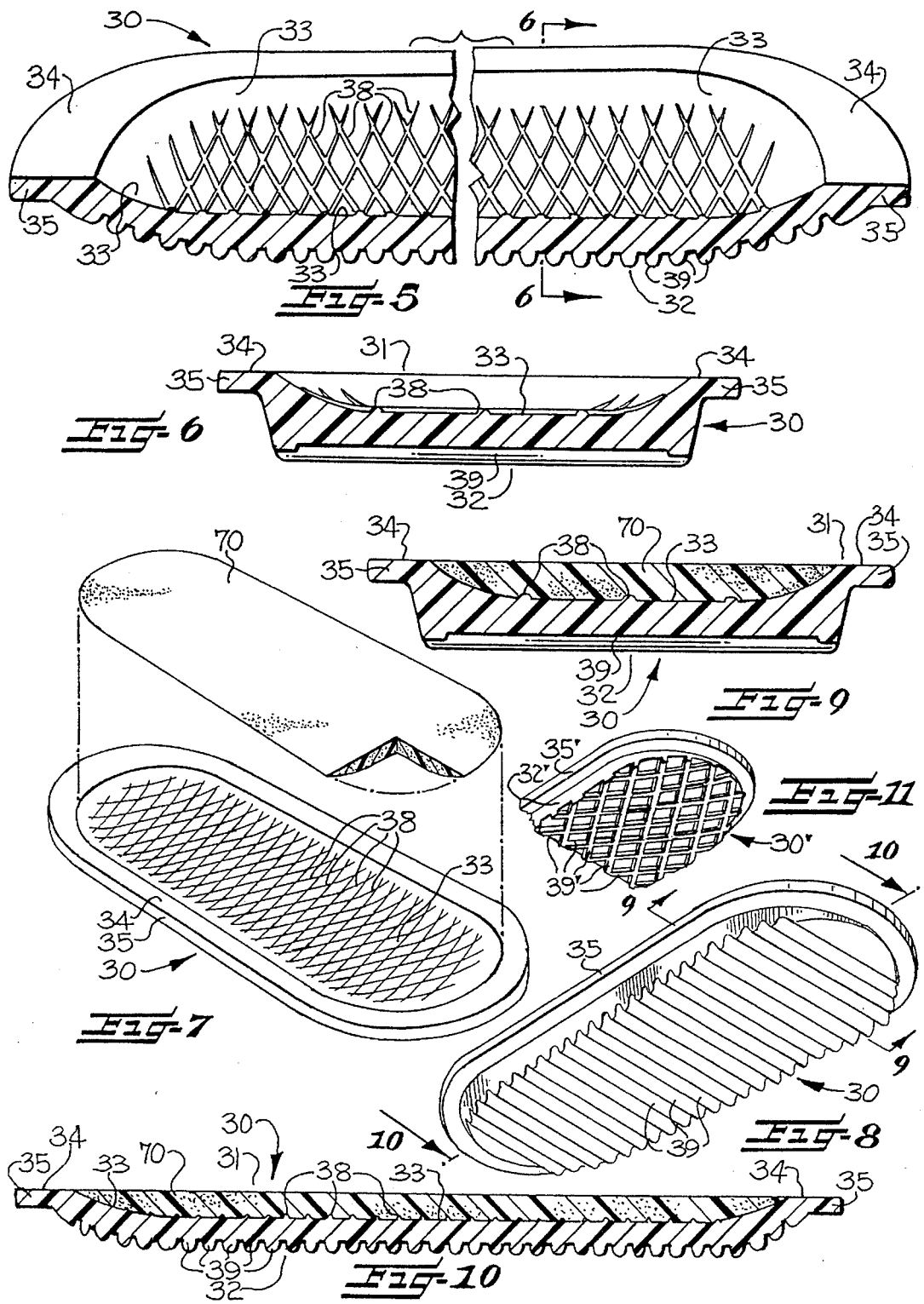

SHOE FOR A FOOT CAST

FIELD OF THE INVENTION

This invention relates to shoes and more particularly to a shoe for receiving a foot cast therein.

BACKGROUND OF THE INVENTION

Often after a person has an accident involving the leg or foot, a physician or other medical personnel places the leg and foot in a cast to keep the injured leg or foot immobile. The casts are usually worn for extended periods of time to enhance the healing process for the injury. Because of the extended period of wearing the cast, the wearer desires to walk about for various reasons. Hence, shoes and other devices for foot casts have been developed to protect the foot cast from being dirtied or damaged from the walking of the wearer.

The shoes for foot casts typically have a sole and a shoe upper connected to the sole. The innersole of these shoes, however, are flat and the relatively rounded lower portions of the foot cast are received onto the flat innersole. This causes the shoe to be unstable and causes a rocking motion within the shoe when worn by the injured person. Also, because of the larger size or downward projecting extent of the foot cast on one foot of the wearer, the gate differential between a normal stride and the stride of the wearer of the foot cast increases. These problems make the foot cast shoe uncomfortable, awkward to wear, and damaging to the hip joint.

Thus, there is a need for a shoe for a foot cast which reduces the rocking of the cast within the shoe and which reduces the gait differential to thereby provide more normal walk for the wearer.

SUMMARY OF THE INVENTION

Therefore, the present invention provides a shoe for reducing the rocking of the cast within the shoe and for reducing the gait differential of the wearer.

More particularly, the shoe has a molded sole formed of a foam material, a shoe upper connected to the molded sole and adapted to extend around the foot cast, and straps connected to the shoe upper for securing the shoe upper and the molded sole on the foot cast. The molded sole is formed of integrally molded foam material wherein an upper portion thereof defines an innersole and a lower portion thereof defines an outersole. The innersole has a concave recess extending throughout major portions thereof and with a depth thereof being such as to receive lower portions of the foot cast and to permit the wearer thereof to have a gait corresponding substantially to that of a normal shoe. The outersole has a roughened outer surface for providing increased frictional resistance with the surface upon which the outersole contacts.

BRIEF DESCRIPTION OF THE DRAWINGS

Some of the objects and advantages of the present invention having been stated, others will become apparent as the description proceeds when taken in conjunction with the accompanying drawings, in which:

FIG. 1 is a perspective view of the shoe for a foot cast according to the present invention;

FIG. 2 is a perspective view of the shoe with a foot cast therein illustrated in phantom lines according to the present invention;

FIG. 3 is a rear elevational view of the shoe with straps extending around a foot cast illustrated in phantom lines;

FIG. 4 ms a longitudinal sectional view of the shoe with straps extending around a foot cast illustrated in phantom lines;

FIG. 5 is a longitudinal sectional perspective view of the molded sole of the shoe according to the present invention;

FIG. 6 ms a transverse sectional view of the molded sole taken substantially along line 6—6 of FIG. 5 and showing the full width of the sole;

FIG. 7 is an exploded view of a second embodiment of the molded sole of the shoe having a fabric layer with parts broken away for clarity in the concave recess of the molded sole;

FIG. 8 is a bottom perspective view of the molded sole of both embodiments of the shoe according to the present invention;

FIG. 9 is a transverse sectional view of the second embodiment of the molded shoe according to the present invention taken along line 9—9 of FIG. 8 and having the fabric layer as illustrated in FIG. 7;

FIG. 10 is a longitudinal sectional view of the second embodiment of the molded shoe according to the present invention taken along line 10—10 of FIG. 8 and having the fabric layer as illustrated in FIG. 7; and FIG. 11 is a fragmentary perspective view of a second embodiment of the outersole of the molded sole according to the present invention.

DESCRIPTION OF THE ILLUSTRATED EMBODIMENTS

The present invention now will be described more fully hereinafter with reference to the accompanying drawings in which preferred embodiments of the invention are shown. Like numbers refer to like elements throughout.

Referring now to the drawings, FIG. 1 is a perspective view of a shoe 20 according to the present invention. The shoe is worn on a foot cast C having a foot F therein, as shown by phantom lines in FIGS. 2–4, and provides a more normal gait as the wearer of the cast C walks. For providing the more normal gait, the shoe 20 has a molded sole 30 formed of a foam material. The molded sole 30 has a relatively light overall weight range of only 3 to 5.5 ounces for encompassing all sizes of shoes 20. A shoe upper 40 connects to the molded sole and is adapted to extend around the foot cast C. As shown in the illustrated embodiment of FIGS. 1–4, the shoe upper 40 has a pair of opposing fabric sections 41, 42 defining an open toe and open heel shoe upper 40. Straps connect to the shoe upper 40 and secure the shoe upper 40 and the molded sole 30 on the foot cast C. It will also be apparent that various other types and styles of shoe uppers may also be used with other embodiments of the invention.

As shown, three separate straps 51, 52, 53 connect respective front, medial, and rear portions of the opposing fabric sections 41, 42 of the shoe upper 40 to each other. The straps 51, 52, 53 and the shoe upper 40 carry fastening means 60 shown in the form of cooperating VELCRO-type fasteners 61, 62, 63 to secure the straps 51, 52, 53 around a foot cast C within the shoe 20 as further shown in FIGS. 2–4. The cooperating VELCRO-type fasteners 61, 62, 63 have one component with hooks and the other component with loops.

The straps 51, 52 extend through and around buckle loops 56, 57 attached to the fabric section 42 to connect the front and medial portions of the fabric section 41, 42. The strap 53 at the rear portion of the fabric section 41, 42 connects to an upper rear portion 58 of the fabric section 42 having a component of the VELCRO-type fastener 63 attached thereto. Other types of shoe uppers having various arrangements of fabric sections or straps may also be used with the embodiments of the molded sole 30 of the shoe 20 the construction of which is described further herein.

The construction of the molded sole 30 of the shoe 20 is further shown in FIGS. 4–10. The molded sole 30 is formed of integrally molded foam material, preferably urethane foam, and has an upper portion thereof defining an innersole 31 and a lower portion thereof defining an outersole 32. The shoe 20 may be constructed in sizes ranging from extra-small to extra large with approximate sole widths, lengths, and weights as shown in the table below.

| Sole Size | Width | Length | Sole Weight |
| --- | --- | --- | --- |
| Extra-Small | 3.5 inches | 7.0 inches | 3.9 ounces |
| Small | 4.25 inches | 9.5 inches | 4.8 ounces |
| Medium | 4.75 inches | 10.5 inches | 6.3 ounces |
| Large | 5.5 inches | 13.0 inches | 8.7 ounces |
| Extra-Large | 5.25 inches | 14.0 inches | 10.5 ounces |

These ranges of sole weights of about 3 to 11 ounces for encompassing the various shoe sizes provide the shoe 20 with a relatively light overall weight which is considerably less than conventional foot cast shoes, preferably about 40% less. The width of the molded sole 30 is generally uniform as shown in the drawings, but may also be wider in the heel region and narrower in the toe region for adapting to fit casts of similar configuration.

The innersole 31 of the molded sole 30 according to the present invention has a concave recess 33 extending throughout major portions thereof and with the depth thereof being such as to receive lower portions of the foot cast C and to permit the wearer thereof to have a gait corresponding substantially to that of a normal shoe. The depth of the recess is such as to bring the foot of into a neutral position within the shoe and provide stability for the wearer. The depth typically ranges from 50–75% of the thickness of the molded sole 30, but it will be apparent to those skilled in the art that the depth and shape may be adjusted according to the size, type of material, and shape of the cast used on the wearers foot.

As shown in FIGS. 1, 5, and 7, the innersole 31 of the molded sole 30 also has an outer peripheral portion having a substantially flat upper surface lying in a common plane and defining a ledge 34 surrounding the outermost extent of the concave recess 33.

The ledge 34 preferably extends completely around the periphery of the molded sole 30, but as apparent to those skilled in the art, the ledge 34 may only extend around portions of the molded sole 34 such as only the front and side portions. The ledge 34 cooperates with the concave recess 33 so as to receive lower outer portions of a foot cast C thereone (FIG. 2) thereby enhancing contact of the shoe.20 with the foot cast C for steadier support of the foot cast C during walking by the wearer of the shoe 20.

In the illustrated embodiments, the ledge 34 surrounding the concave recess 33 has a reduced thickness molded portion extending around the perimeter of the ledge 34 defining a welt 35. A narrow width covering fabric 36 (FIGS. 1–4) extends around and encases the welt 35. Stitching 37, as best shown in FIGS. 1 and 2, extends along and through the welt 35 and connects the welt 35 to the shoe upper 40 and the narrow width covering fabric 36. In other embodiments, the shoe upper 40 may connect to the molded sole 30 by molding the shoe upper 40 to the molded sole 30, directly or indirectly, so as to eliminate the need for sewing or having the welt 35 as described above.

In a first embodiment of the molded sole 30, as shown in FIGS. 1, 5, 6, and 8, the innersole 31 further has a rough non-smooth upper surface on the concave recess 33 for increasing frictional engagement with a foot cast C and for reducing slippage of a foot cast C when engaging the innersole 31. The rough non-smooth upper surface in these views is shown in the form of diamond-shaped crisscross pattern 38 extending along the upper surface. Other forms of a rough non-smooth upper surface 38, such as a pebbled surface or pattern, apparent to those skilled in the art may also be used.

In a second embodiment of the molded sole 30, as shown in FIGS. 7–10, the rough non-smooth upper surface 38 of the innersole 31 has a hydrophobic fabric layer 70 positioned in the concave recess 33 for wicking away and reducing accumulation of moisture within the concave recess 33. The hydrophobic fabric layer is cut in the shape of the concave recess 33 and is preferably adhesively sealed into the recess 33. It will be apparent to those skilled in the art that the hydrophobic fabric layer 70 may extend to and overlie the ledge 34 of the innersole 31.

The first and second embodiments of the outersole 32 and 32' of the invention, as best shown in FIGS. 4, 5, 8, 10, and 11, have a roughened outer surface for providing increased frictional resistance with the surface upon which the outersole 32 and 32' contacts. In a first embodiment, ash shown in FIGS. 4, 5, 8, and 10, the roughened outer surface of the outersole 32 is shown in the form of closely adjacent ribs 39 transversely arranged to the lengthwise extent of the shoe 20. In a second embodiment of the outersole 32'0 of the molded sole 30, the roughened outer surface is shown in the form of a raised diamond-shaped criss-cross pattern 39' extending the length of the outer surface. Other forms of a roughened outer surface apparent to those skilled in the art may also be used.

In the drawings and specification, there have been disclosed preferred embodiments of the invention and, although specific terms are employed, they are used in a generic and descriptive sense only and not for the purposes of limitation, the scope of the invention being set forth in the following claims.

That which is claimed is:

1. A shoe to be worn on a foot cast for providing a more normal gait as the wearer of the cast walks and for reducing rocking action caused by the foot cast interfacing with an innersole of a shoe, said shoe comprising a molded sole formed of a foam material, a shoe upper connected to said molded sole and adapted to extend around the foot cast, and straps connected to said shoe upper for securing said shoe upper and said molded sole on the foot cast, and wherein said molded sole is formed of integrally molded foam material with an upper portion thereof defining an innersole and a lower portion thereof defining an outersole, said innersole having a concave recess integrally molded therein and extending throughout major portions and with the depth thereof being sufficient to receive lower portions of the foot cast and to permit the wearer thereof to have a gait corresponding substantially to that of a normal shoe, said innersole further having a substantially flat upper surface lying in a common plane and defining a ledge surrounding said concave recess, said ledge having portions positioned within said shoe upper and other portions positioned outside said shoe upper, at least portions of said ledge positioned within said shoe upper cooperating with said concave recess so as to receive lower outer portions of a foot cast thereon, thereby enhancing contact of the shoe with the foot cast for steadier support of the foot cast during walking by the wearer of the shoe, said outersole having a roughened outer surface for providing increased frictional resistance with the surface upon which the outersole contacts.

2. A shoe according to claim 1, wherein said innersole further comprises a hydrophobic fabric layer positioned in said concave recess for wicking away and reducing accumulation of moisture within said concave recess.

3. A shoe according to claim 1, wherein said innersole further comprises a rough non-smooth upper surface on said concave recess for increasing frictional engagement with a foot cast and for reducing slippage of a foot cast when engaging said innersole.

4. A shoe according to claim 1, wherein said ledge surrounding said concave recess further comprises a reduced thickness molded portion extending around the perimeter of said ledge and defining a welt, and stitching connecting said shoe upper to said welt.

5. A shoe according to claim 1, further comprising cooperating fastening means carried by said straps and said shoe upper for securing said straps around a foot cast when within the shoe.

6. A shoe according to claim 5, wherein said cooperating fastening means comprises fasteners wherein one component has hooks and the other component has loops.

7. A shoe according to claim 1, wherein said roughened outer surface of said outersole comprises closely adjacent ribs transversely arranged to the lengthwise extent of the shoe.

8. A shoe according to claim 1, wherein said foam material of said molded shoe comprises urethane foam.

9. A shoe according to claim 1, wherein said molded sole has a relatively light overall weight range of only about 3 to 11 ounces for encompassing all sizes of shoes.

10. A shoe according to claim 1, wherein said molded sole further comprises a reduced thickness molded portion defining a welt along the periphery of said molded sole, a narrow width covering fabric extending around and encasing said welt, and stitching extending along and through said welt and connecting the welt to said shoe upper and said narrow width covering fabric.

11. A shoe according to claim 1, wherein said shoe upper comprises a pair of opposing fabric sections defining an open toe and open heel shoe upper, and wherein said straps connected to said shoe upper include straps connecting respective front, medial, and rear portions of said opposing fabric sections to each other.

12. A shoe to be worn on a foot cast for providing a more normal gait as the wearer of the cast walks and for reducing rocking action caused by the foot cast interfacing with an innersole of a shoe, said shoe comprising a molded sole formed of a foam material having a relatively light overall weight range of only about 3 to 11 ounces for encompassing all sizes of shoes, a shoe upper connected to said molded sole and adapted to extend around the foot cast, and straps connected to said shoe upper for securing said shoe upper and said molded sole on the foot cast, and wherein said molded sole is formed of integrally molded foam material with an upper portion thereof defining an innersole and a lower portion thereof defining an outersole, said innersole having a concave recess integrally molded therein and extending throughout major portions and with the depth thereof being sufficient to receive lower portions of the foot cast and to permit the wearer thereof to have a gait corresponding substantially to that of a normal shoe, an outer peripheral portion of said innersole having a substantially flat upper surface lying in a common plane and defining a ledge surrounding the outermost extent of said concave recess, said ledge having portions positioned within said shoe upper and other portions positioned outside said shoe upper, at least portions of said ledge positioned within said shoe upper cooperating with said concave recess so as to receive lower outer portions of a foot cast thereon thereby enhancing contact of the shoe with the foot cast for steadier support of a foot cast during walking by the wearer of the shoe, said ledge surrounding said concave recess further comprising a reduced thickness molded portion extending around a perimeter of said ledge and defining a welt, and stitching connecting said shoe upper to said welt, said outersole having a roughened outer surface for providing increased frictional resistance with the surface upon which the outersole contacts.

13. A shoe according to claim 12, wherein said innersole further comprises a hydrophobic fabric layer positioned in said concave recess for wicking away and reducing accumulation of moisture within said concave recess.

14. A shoe according to claim 12, wherein said innersole further comprises a rough non-smooth upper surface on said concave recess for increasing frictional engagement with a foot cast and for reducing slippage of a foot cast when engaging said innersole.

15. A shoe according to claim 12, further comprising cooperating fasteners carried by said straps and said shoe upper wherein one component has hooks and the other component has loops for securing said straps around a foot cast when within the shoe.

16. A shoe according to claim 12, wherein said shoe upper comprises a pair of opposing fabric sections defining an open toe and open heel shoe upper, and wherein said straps connected to said shoe upper include straps connecting respective front, medial, and rear portions of said opposing fabric sections to each other.

* * * * *